United States Patent [19]

Holmwood et al.

[11] Patent Number: 4,652,579

[45] Date of Patent: Mar. 24, 1987

[54] ANTIMICROBIAL AZOLES

[75] Inventors: Graham Holmwood, Wuppertal; Karl H. Büchel, Burscheid; Manfred Plempel; Ingo Haller, both of Wuppertal, all of Fed. Rep. of Germany

[73] Assignee: Bayer Aktiengesellschaft, Leverkusen, Fed. Rep. of Germany

[21] Appl. No.: 663,012

[22] Filed: Oct. 19, 1984

Related U.S. Application Data

[60] Continuation of Ser. No. 418,937, Sep. 16, 1982, abandoned, which is a division of Ser. No. 256,741, Apr. 23, 1981, abandoned.

[30] Foreign Application Priority Data

May 16, 1980 [DE] Fed. Rep. of Germany ....... 3018865

[51] Int. Cl.$^4$ .................... A01N 43/50; A01N 43/653
[52] U.S. Cl. .................................. 514/383; 514/399; 548/262; 548/341
[58] Field of Search ................................ 514/383, 399

[56] References Cited

U.S. PATENT DOCUMENTS

| | | | |
|---|---|---|---|
| 4,123,542 | 10/1978 | Walker | 548/341 |
| 4,381,306 | 4/1983 | Regel et al. | 548/262 |
| 4,414,210 | 11/1983 | Miller et al. | 548/262 |
| 4,551,469 | 11/1985 | Parry et al. | 548/262 |

FOREIGN PATENT DOCUMENTS

| | | | |
|---|---|---|---|
| 0015746 | 9/1980 | European Pat. Off. | 548/262 |
| 2623129 | 11/1977 | Fed. Rep. of Germany | 548/341 |
| 2737489 | 2/1978 | Fed. Rep. of Germany | 548/341 |
| 2908378 | 9/1980 | Fed. Rep. of Germany | 548/262 |

*Primary Examiner*—Richard L. Raymond
*Attorney, Agent, or Firm*—Sprung, Horn, Kramer & Woods

[57] ABSTRACT

The invention relates to 1-hydroxyethyl-azole derivatives of formula (I) in composition form and includes the use of such compositions as antimicrobial agents.

6 Claims, No Drawings

ANTIMICROBIAL AZOLES

This is a continuation of application Ser. No. 418,937, filed Sept. 16, 1982, which is a division of Ser. No. 256,741, filed Apr. 23, 1981, both now abandoned.

The present invention relates to the use as antimicrobial agents, in particular as antimycotic agents, of certain new 1-hydroxyethyl-azole derivatives.

It has already been disclosed that tertiary imidazolyl alcohols, such as 1,2-bis(4-chlorophenyl)-3-(imidazol-1-yl)-2-propanol, have good antimycotic properties (see DE-OS (German Published Specification) No. 3,623,129). However, their action is not always completely satisfactory.

It has also been disclosed that 1-(β-aryl)-ethylimidazole derivatives, such as, in particular, 1-[2,4-dichloro-β-(2,4-dichlorobenzyloxy)-phenethyl]-imidazole nitrate (miconazole), have a good antimycotic action (see DE-AS (German Published Specification) No. (1,940,388). However, this action is not always satisfactory in vivo, such as, in particular, against Candida.

According to the present invention there are provided pharmaceutical composition containing as an active ingredient a compound which is a 1-hydroxyethyl-azole derivative of the formula

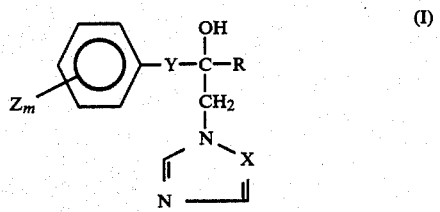

or a physiologically acceptable acid addition salt thereof, in which

R represents an alkyl radical, an optionally substituted cycloalkyl radical or an optionally substituted phenyl radical, X represents a nitrogen atom or a CH group, Y represents a grouping —OCH$_2$—, —CH$_2$CH$_2$— or —CH=CH—, each Z independently represents a halogen atom, an alkyl, cycloalkyl, alkoxy, alkylthio, halogenoalkyl, halogenoalkoxy or halogenoalkylthio radical, an optionally substituted phenyl radical, an optionally substituted phenoxy radical, an optionally substituted phenylalkyl radical or an optionally substituted phenylalkoxy radical and m is 0, 1, 2, or 3, in admixture with an inert pharmaceutical carrier, e.g. a solid or liquid gaseous diluent, or in a mixture with a liquid diluent other than a solvent of a molecular weight less than 200 except in the presence of a surface active agent.

The compositions of the present invention have good antimicrobial properties, in particular good antimycotic properties.

As used herein and unless other specified, the term "alkyl" (or alkyl moieties) preferably contain 1 to 8 (particularly 1 to 4) carbon atoms, the term "cycloalkyl" preferably contains 3 to 7 (particularly 5 to 6) ring members; the term "halogen" preferably includes chlorine, bromine and fluorine; the terms "alkoxy" and "alkylthio" preferably contain 1 to 8 (particularly 1 to 4) carbon atoms; the terms "halogenoalkyl", "halogenealkoxy" and "halogenoalkylthio" preferably contain fluorine or chlorine as the halogen, contain an alkyl portion having 1 to 2 carbon atoms and are particularly "perhalogenoalkyl", "perhalogenoalkoxy" or "perhalogenoalkylthio".

The compounds of the formula (I) have an asymmetric carbon atom and can therefore be obtained in the two optical isomer forms. If Y represents the grouping —OH=OH—, the compounds of the formula (I) can additionally exist in two geometric isomer forms. The present invention relates to compositions comprising both the isomer mixtures and the individual isomers.

Surprisingly, the 1-hydroxyethyl-azole derivatives according to the invention exhibit a better antimycotic action spectrum than 1,2-bis(4-chlorophenyl)-3-(imidazol-1-yl)-2-propanol, which is known from the state of the art, and, in particular, a better therapeutically useful in vivo activity than 1 [2,4-dichloro-β-(2,4-dichlorobenzyloxy)-phenethyl]-imidazole nitrate, which is known from the state of the art and is recognised as a good agent of the same type of action. The use of the active compounds according to the invention thus represents a valuable enrichment of pharmacy.

Preferred compounds for use according to the present invention are those in which R represents a straight-chain or branched alkyl radical with 1 to 4 carbon atoms, a cycloalkyl radical which has 3 to 7 (preferably 5 to 6) carbon atoms and is optionally substituted by alkyl with 1 or 2 carbon atoms, or a phenyl radical which is optionally monosubstituted, disubstituted, trisubstituted or further polysubstituted by identical or different substituents, preferred possible substituents being; halogen, alkyl with 1 to 4 carbon atoms and halogenoalkyl (preferably perhalogenoalkyl, such as perfluoromethyl) with 1 or 2 carbon atoms and 1 to 5 identical or different halogen atoms (such as, preferably fluorine and chlorine atoms), each Z independently represents a halogen (preferably chlorine or bromine) atom, a straight-chain or branched alkyl radical with 1 to 4 carbon atoms, a cycloalkyl radical with 5 to 7 carbon atoms, an alkoxy or alkylthio radical with in each case 1 to 4 carbon atoms, a halogenoalkyl, halogenoalkoxy or halogenoalkylthio radical (each being preferably perhalogeno in which the halogen atoms are fluorine atoms) with in each case 1 or 2 carbon atoms and 1 to 5 identical or different halogen atoms (such as, preferably, fluorine and chlorine atoms), or represents an optionally substituted phenyl or phenoxy radical or a phenylalkyl or phenylalkoxy radical, each with 1 or 2 carbon atoms in the alkyl part, preferred substituents which may be mentioned being: halogen (preferably chlorine and bromine) and alkyl with 1 to 4 carbon atoms, and X, Y and m have the abovementioned meanings.

Particularly preferred compounds for use according to the present invention are those in which R represents a tert.-butyl, isopropyl or methyl radical; a cyclopropyl, cyclopentyl or cyclohexyl radical (in each case optionally methyl-substituted); or a phenyl radical which is optionally monosubstituted or disubstituted by identical or different substituents selected from fluorine, chlorine, methyl and trifluoromethyl; each Z independently represents a fluorine, chlorine or bromine atom or a methyl, tert.-butyl, cyclohexyl, methoxy, methylthio, trifluoromethyl, trifluoromethoxy or trifluoroacethylthio radical, or a phenyl phenoxy, benzyl or benzyloxy radical (in each case optionally monosubstituted or disubstituted by identical or different substituents selected from fluorine, chlorine and methyl); and X, Y and m have the abovementioned meanings.

The following compounds of the formula (I) may be mentioned specifically for use according to the present invention, in addition to the compounds mentioned in the preparation Examples:

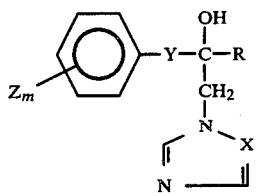
(I)

| $Z_m$ | Y | R | X |
|---|---|---|---|
| 4-C₆H₅ | —O—CH₂— | —C(CH₃)₃ | N(CH) |
| 4-(C₆H₄)—Cl | " | " | " |
| 4-O—C₆H₅ | " | " | " |
| 4-O—(C₆H₄)—Cl | " | " | " |
| 4-CH₂—C₆H₅ | " | " | " |
| 4-CH₂—(C₆H₄)—Cl | " | " | " |
| 4-O—CH₂—C₆H₅ | " | " | " |
| 4-O—CH₂—(C₆H₄)—Cl | " | " | " |
| 3,4-Cl₂ | " | " | " |
| 4-CF₃ | " | " | " |
| 4-OCF₃ | " | " | " |
| 4-SCF₃ | " | " | " |
| 4-SCH₃ | " | " | " |
| 4-C(CH₃)₃ | " | " | " |
| 4-C₆H₅ | —O—CH₂ | —(C₆H₄)—Cl | " |
| 4-(C₆H₄)—Cl | " | " | " |
| 4-O—C₆H₅ | " | " | " |
| 4-O—(C₆H₄)—Cl | " | " | " |
| 4-CH₂—C₆H₅ | " | " | " |
| 4-CH₂—(C₆H₄)—Cl | " | " | " |
| 4-O—CH₂—C₆H₅ | " | " | " |
| 4-O—CH₂—(C₆H₄)—Cl | " | " | " |
| 3,4-Cl₂ | " | " | " |
| 4-CF₃ | " | " | " |
| 4-OCF₃ | " | " | " |
| 4-SCF₃ | " | " | " |
| 4-SCH₃ | " | " | " |
| 4-C(CH₃)₃ | " | " | " |
| 4-C₆H₅ | —O—CH₂— | —CH(CH₃)₂ | " |
| 4-(C₆H₄)—Cl | " | " | " |
| 4-O—C₆H₅ | " | " | " |
| 4-O—(C₆H₄)—Cl | " | " | " |
| 4-CH₂—C₆H₅ | " | " | " |
| 4-CH₂—(C₆H₄)—Cl | " | " | " |
| 4-O—CH₂—C₆H₅ | " | " | " |
| 4-O—CH₂—(C₆H₄)—Cl | " | " | " |
| 3,4-Cl₂ | " | " | " |
| 4-CF₃ | " | " | " |
| 4-OCF₃ | " | " | " |
| 4-SCF₃ | " | " | " |
| 4-SCH₃ | " | " | " |
| 4-C(CH₃)₃ | " | " | " |
| 4-C₆H₅ | " | —(C₆H₅) | " |
| 4-(C₆H₄)—Cl | " | " | " |
| 4-O—C₆H₅ | " | " | " |

-continued $$\text{(I)}$$

Structure: Phenyl ring with $Z_m$ substituent, connected to $Y-C(OH)(R)-CH_2-N$ where N is part of a triazole ring (N=CH-N-CH=, with X on the ring).

| $Z_m$ | Y | R | X |
|---|---|---|---|
| 4-O-C₆H₄-Cl | " | " | " |
| 4-CH₂-C₆H₅ | " | " | " |
| 4-CH₂-C₆H₄-Cl | " | " | " |
| 4-O-CH₂-C₆H₅ | " | " | " |
| 4-O-CH₂-C₆H₄-Cl | " | " | " |
| 3,4-Cl₂ | " | " | " |
| 4-CF₃ | " | " | " |
| 4-OCF₃ | " | " | " |
| 4-SCF₃ | " | " | " |
| 4-SCH₃ | " | " | " |
| 4-C(CH₃)₃ | " | " | " |
| 4-C₆H₅ | " | cyclopropyl-CH₃ | " |
| 4-C₆H₄-Cl | " | " | " |
| 4-O-C₆H₅ | " | " | " |
| 4-O-C₆H₄-Cl | " | " | " |
| 4-CH₂-C₆H₅ | " | " | " |
| 4-CH₂-C₆H₄-Cl | " | " | " |
| 4-O-CH₂-C₆H₅ | " | " | " |
| 4-O-CH₂-C₆H₄-Cl | " | " | " |
| 3,4-Cl₂ | " | " | " |
| 4-CF₃ | " | " | " |
| 4-OCF₃ | " | " | " |
| 4-SCF₃ | " | " | " |
| 4-SCH₃ | " | " | " |
| 4-C(CH₃)₃ | " | " | " |

-continued $$\text{(I)}$$

| $Z_m$ | Y | R | X |
|---|---|---|---|
| 4-C₆H₅ | —CH₂—CH₂— | —C(CH₃)₃ | " |
| 4-C₆H₄-Cl | " | " | " |
| 4-O-C₆H₅ | " | " | " |
| 4-O-C₆H₄-Cl | " | " | " |
| 4-CH₂-C₆H₅ | " | " | " |
| 4-CH₂-C₆H₄-Cl | " | " | " |
| 4-O-CH₂-C₆H₅ | " | " | " |
| 4-O-CH₂-C₆H₄-Cl | " | " | " |
| 3,4-Cl₂ | " | " | " |
| 4-CF₃ | " | " | " |
| 4-OCF₃ | " | " | " |
| 4-SCF₃ | " | " | " |
| 4-SCH₃ | " | " | " |
| 4-C(CH₃)₃ | " | " | " |
| 4-C₆H₅ | " | " | C₆H₄-Cl |
| 4-C₆H₄-Cl | " | " | " |
| 4-O-C₆H₅ | " | " | " |
| 4-O-C₆H₄-Cl | " | " | " |
| 4-CH₂-C₆H₅ | " | " | " |
| 4-CH₂-C₆H₄-Cl | " | " | " |
| 4-O-CH₂-C₆H₅ | " | " | " |
| 4-O-CH₂-C₆H₄-Cl | " | " | " |

-continued

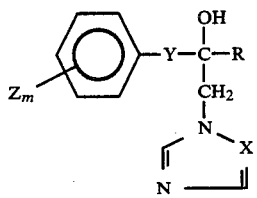

(I)

| $Z_m$ | Y | R | X |
|---|---|---|---|
| 3,4-Cl$_2$ | " | " | " |
| 4-CF$_3$ | " | " | " |
| 4-OCF$_3$ | " | " | " |
| 4-SCF$_3$ | " | " | " |
| 4-SCH$_3$ | " | " | " |
| 4-C(CH$_3$)$_3$ | " | " | " |
| 4-C$_6$H$_5$ | " | —CH(CH$_3$)$_2$ | " |
| 4-C$_6$H$_4$-Cl | " | " | " |
| 4-O-C$_6$H$_5$ | " | " | " |
| 4-O-C$_6$H$_4$-Cl | " | " | " |
| 4-CH$_2$-C$_6$H$_5$ | " | " | " |
| 4-CH$_2$-C$_6$H$_4$-Cl | " | " | " |
| 4-O-CH$_2$-C$_6$H$_5$ | " | " | " |
| 4-O-CH$_2$-C$_6$H$_4$-Cl | " | " | " |
| 3,4-Cl$_2$ | " | " | " |
| 4-CF$_3$ | " | " | " |
| 4-OCF$_3$ | " | " | " |
| 4-SCF$_3$ | " | " | " |
| 4-SCH$_3$ | " | " | " |
| 4-C(CH$_3$)$_2$ | " | " | " |
| 4-C$_6$H$_5$ | " | —C$_6$H$_{11}$ | " |
| 4-C$_6$H$_4$-Cl | " | " | " |
| 4-O-C$_6$H$_5$ | " | " | " |
| 4-O-C$_6$H$_4$-Cl | " | " | " |
| 4-CH$_2$-C$_6$H$_5$ | " | " | " |
| 4-CH$_2$-C$_6$H$_4$-Cl | " | " | " |

-continued

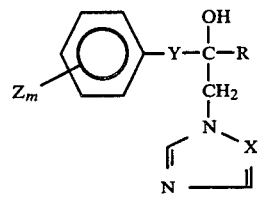

(I)

| $Z_m$ | Y | R | X |
|---|---|---|---|
| 4-O-CH$_2$-C$_6$H$_5$ | " | " | " |
| 4-O-CH$_2$-C$_6$H$_4$-Cl | " | " | " |
| 3,4-Cl$_2$ | " | " | " |
| 4-CF$_3$ | " | " | " |
| 4-OCF$_3$ | " | " | " |
| 4-SCF$_3$ | " | " | " |
| 4-SCH$_3$ | " | " | " |
| 4-C(CH$_3$)$_3$ | " | " | " |
| 4-C$_6$H$_5$ | " | cyclopropyl-CH$_3$ | " |
| 4-C$_6$H$_4$-Cl | " | " | " |
| 4-O-C$_6$H$_5$ | " | " | " |
| 4-O-C$_6$H$_4$-Cl | " | " | " |
| 4-CH$_2$-C$_6$H$_5$ | " | " | " |
| 4-CH$_2$-C$_6$H$_4$-Cl | " | " | " |
| 4-O-CH$_2$-C$_6$H$_5$ | " | " | " |
| 4-O-CH$_2$-C$_6$H$_4$-Cl | " | " | " |
| 3,4-Cl$_2$ | " | " | " |
| 4-CF$_3$ | " | " | " |
| 4-OCF$_3$ | " | " | " |
| 4-SCF$_3$ | " | " | " |
| 4-SCH$_3$ | " | " | " |
| 4-C(CH$_3$)$_3$ | " | " | " |
| 4-C$_6$H$_5$ | —CH=CH— | —C(CH$_3$)$_3$ | " |
| 4-C$_6$H$_4$-Cl | " | " | " |
| 4-O-C$_6$H$_5$ | " | " | " |

-continued $$\text{Structure (I): } Z_m\text{-C}_6H_4\text{-Y-C(OH)(R)-CH}_2\text{-N(ring with N, X)}$$

| $Z_m$ | Y | R | X |
|---|---|---|---|
| 4-O-C6H4-Cl | " | " | " |
| 4-CH2-C6H5 | " | " | " |
| 4-CH2-C6H4-Cl | " | " | " |
| 4-O-CH2-C6H5 | " | " | " |
| 4-O-CH2-C6H4-Cl | " | " | " |
| 3,4-Cl2 | " | " | " |
| 4-CF3 | " | " | " |
| 4-OCF3 | " | " | " |
| 4-SCF3 | " | " | " |
| 4-SCH3 | " | " | " |
| 4-C(CH3)3 | " | " | " |
| 4-C6H5 | " | 4-C6H4-Cl | " |
| " | " | " | " |
| 4-C6H4-Cl | " | " | " |
| 4-O-C6H5 | " | " | " |
| 4-O-C6H4-Cl | " | " | " |
| 4-CH2-C6H5 | " | " | " |
| 4-CH2-C6H4-Cl | " | " | " |
| 4-O-CH2-C6H5 | " | " | " |
| 4-O-CH2-C6H4-Cl | " | " | " |
| 3,4-Cl2 | " | " | " |
| 4-CF3 | " | " | " |
| 4-OCF3 | " | " | " |
| 4-SCF3 | " | " | " |
| 4-SCH3 | " | " | " |
| 4-C(CH3)3 | " | " | " |
| " | " | —CH(CH3)2 | " |
| 4-C6H5 | " | " | " |

| $Z_m$ | Y | R | X |
|---|---|---|---|
| 4-C6H4-Cl | " | " | " |
| 4-O-C6H5 | " | " | " |
| 4-O-C6H4-Cl | " | " | " |
| 4-CH2-C6H5 | " | " | " |
| 4-CH2-C6H4-Cl | " | " | " |
| 4-O-CH2-C6H5 | " | " | " |
| 4-O-CH2-C6H4-Cl | " | " | " |
| 3,4-Cl2 | " | " | " |
| 4-CF3 | " | " | " |
| 4-OCF3 | " | " | " |
| 4-SCF3 | " | " | " |
| 4-SCH3 | " | " | " |
| 4-C(CH3)3 | " | " | " |
| 4-C6H5 | " | H | " |
| " | " | " | " |
| 4-C6H4-Cl | " | " | " |
| 4-O-C6H5 | " | " | " |
| 4-O-C6H4-Cl | " | " | " |
| 4-CH2-C6H5 | " | " | " |
| 4-CH2-C6H4-Cl | " | " | " |
| 4-O-CH2-C6H5 | " | " | " |
| 4-O-CH2-C6H4-Cl | " | " | " |
| 3,4-Cl2 | " | " | " |
| 4-CF3 | " | " | " |
| 4-OCF3 | " | " | " |

-continued $$\text{(I)}$$

[Structure: Z_m-substituted phenyl—Y—C(OH)(R)—CH2—N(triazole/imidazole with X)]

| $Z_m$ | Y | R | X |
|---|---|---|---|
| 4-SCF₃ | " | " | " |
| 4-SCH₃ | " | " | " |
| 4-C(CH₃)₃ | " | " | " |
| 4-C₆H₅ | " | " | " |
| 4-C₆H₅ | " | cyclopropyl-CH₃ | " |
| 4-(4-Cl-C₆H₄) | " | " | " |
| 4-O-C₆H₅ | " | " | " |
| 4-O-(4-Cl-C₆H₄) | " | " | " |
| 4-CH₂-C₆H₅ | " | " | " |
| 4-CH₂-(4-Cl-C₆H₄) | " | " | " |
| 4-O-CH₂-C₆H₅ | " | " | " |
| 4-O-CH₂-(4-Cl-C₆H₄) | " | " | " |
| 3,4-Cl₂ | " | " | " |
| 4-CF₃ | " | " | " |
| 4-OCF₃ | " | " | " |
| 4-SCF₃ | " | " | " |
| 4-SCH₃ | " | " | " |
| 4-C(CH₃)₃ | " | " | " |
| 4-Cl | —O—CH₂— | —CH(CH₃)₂ | " |
| 4-F | " | " | " |
| 4-CH₃ | " | " | " |
| 4-Cl | " | cyclohexyl-H | " |
| 4-F | " | " | " |
| 4-CH₃ | " | " | " |
| 4-Cl | " | cyclopropyl-CH₃ | " |
| 4-F | " | " | " |
| 4-CH₃ | " | " | " |
| 4-Cl | —CH₂—CH₂— | —CH(CH₃)₂ | " |
| 4-F | " | " | " |
| 4-CH₃ | " | " | " |
| 4-Cl | " | cyclohexyl-H | " |
| 4-F | " | " | " |

-continued $$\text{(I)}$$

| $Z_m$ | Y | R | X |
|---|---|---|---|
| 4-CH₃ | " | " | " |
| 4-Cl | " | cyclopropyl-CH₃ | " |
| 4-F | " | " | " |
| 4-CH₃ | " | " | " |
| 4-Cl | —CH=CH— | —CH(CH₃)₂ | " |
| 4-F | " | " | " |
| 4-CH₃ | " | " | " |
| 4-Cl | " | cyclohexyl-H | " |
| 4-F | " | " | " |
| 4-CH₃ | " | " | " |
| 4-Cl | " | cyclopropyl-CH₃ | " |
| 4-F | " | " | " |
| 4-CH₃ | " | " | " |
| 2,4-Cl₂ | —CH₂—CH₂— | —C(CH₃)₃ | " |
| 4-CH₃ | " | " | " |
| 4-Cl, 2-CH₃ | " | " | " |
| 2,4-Cl₂ | —CH=CH— | " | " |
| 4-CH₃ | " | " | " |
| 4-Cl, 2-CH₃ | " | " | " |
| 4-F | —O—CH₂— | " | " |
| 2-CH₃ | —CH₃—CH₃— | " | N |
| 4-F | —CH=CH— | " | N |

The active compounds and acid addition salts thereof to be used according to the invention are novel. However, they can be prepared by a process in which an oxirane of the formula $$\text{(II)}$$

[Structure showing Z_m-phenyl—Y—C(R)(—O—CH₂—) epoxide]

in which

R, Y, Z and m have the abovementioned meanings, is reacted with an azole of the general formula $$\text{(III)}$$

[Structure: H-N with adjacent N and X in azole ring]

in which

X has the abovementioned meaning, in the presence of an inert organic solvent (such as ethanol), and, optionally, in the presence of a base (such as sodium ethylate), optionally under a pressure from 1 to 25 bars, at a temperature between 60° and 150° C. The end products are isolated in the generally customary manner.

The oxiranes of the formula (II) are novel. They are obtained by a process in which a corresponding ketone of the formula

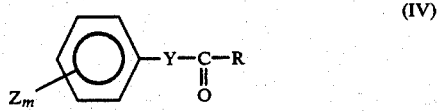

in which

R, Y, Z and m have the abovementioned meanings, (α) is reacted with dimethyloxosulphonium methylide of the formula

in a manner which is in itself known, in the presence of a diluent (such as dimethylsulphoxide) at a temperature between 20° and 80° C. (in this context, compare also the statements in J. Am. Chem. Soc. 87, 1363–1364 (1965), or (β) is reacted with trimethylsulphonium methyl-sulphate of the formula

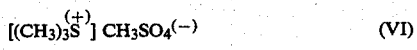

in a manner which is in itself known, in the presence of an inert organic solvent (such as acetonitrile), and in the presence of a base (such as sodium methylate), at a temperature between 0° and 60° C., preferably at room temperature (compare also the statement in Heterocycles 8 397, (1977)).

The oxiranes of the formula (II) thus obtained can, if appropriate, be further reacted directly without being isolated.

The ketones of the formula (IV) are known (see, for example, German Patent Specification No. 2,201,063, DE-OS (German Published Specification) No. 2,705,678. DE-OS (German Published Specification) No. 2,737,489, Tetrahedron 1975, 31, 3 and C.A. 84, 73 906 u), or they can be obtained by the processes described in these references.

Dimethyloxosulphonium methylide of the formula (V) is likewise known, and is employed as a product produced in situ by reacting trimethyloxosulphonium iodide with sodium hydride (see also the abovementioned literature references) or sodium amide. Trimethylsulphonium methylsulphate of the formula (VI) is also known and is employed as a product produced in situ by reacting dimethyl sulphide with dimethyl sulphate (see also the abovementioned literature references).

The azoles of the formula (III) are generally known compounds of organic chemistry.

The following acids can preferably be used for the preparation of physiologically acceptable acid addition salts of the compounds of the formula (I): the hydrogen halide acids (such as hydrobromic acid or, preferably, hydrochloric acid), phosphoric acid, nitric acid, sulphuric acid, monofunctional and bifunctional carboxylic acid and hydroxycarboxylic acids (such as acetic acid, maleic acid, succinic acid, fumeric acid, tartaric acid, tartaric acid, citric acid, salicylic acid, sorbic acid and lactic acid) and sulphonic acids (such as p-toluenesulphonic acid and 1,5-naphthalenedisulphonic acid).

The acid addition salts of the compounds of the formula (I) can be obtained in a simple manner by customary salt formation methods, for example by dissolving a compound of the formula (I) in a suitable inert solvent and adding the acid, for example hydrochloric acid, and they can be isolated in a known manner, for exaample by filtration, and if appropriate purified by washing with an inert organic solvent.

The compounds of the formula (I) which can be used according to the invention and their acid addition salts display antimicrobial actions, in particular powerful antimycotic actions. They possess a very broad antimycotic action spectrum, especially against dermatophytes and blastomyces as well as biphase fungi, for example against varietics of Candida, such as *Candida albicans*, varieties of Epidermophyton, such as *Epidermophyter floccosum*, varieties of Aspergillus, such as *Aspargillus niger* and *Aspergillus fumigatus*, as varieties of Trichophyton, such as *Trichophyton mentagrophytes*, varieties of Microsporon, such as *Microsporon felireum* and varieties of Penicillium, such as *Penicillium commune*. This listing of these micro-organisms in no way implies a limitation of the germs which can be combated but is only of illustrative character.

Examples which may be mentioned of fields of indication in medicine are: dermatomycoses and systemic mycoses caused by *Trichophyton mentagrophytes* and other varieties of Trichophyton, varieties of Microsporon, *Epidermophyton fluoccosum*, blastomyces and biphase fungi as well as moulds.

As stated above, the invention also relates to the use in medicine of the compounds of the invention.

The present invention provides pharmaceutical compositions containing as active ingredient a compound of the invention in admixture with an inert pharmaceutical carrier, e.g. a solid or liquefied gaseous diluent, or in admixture with a liquid diluent other than a solvent of a molecular weight less than 200 (preferably less than 350) except in the presence of a surface active agent.

The invention further provides pharmaceutical compositions containing as active ingredient a compound of the invention in the form of a sterile and/or physiologically isotonic aqueous solution.

The invention also provides medicaments in dosage unit form comprising a compound of the invention.

The invention also provides medicaments in the form of tablets (including lozenges and granules), dragees, capsules, pills, ampoules or suppositories comprising a compound of the invention.

"Medicament" as used in this Specification means physically discrete coherent portions suitable for medical administration. "Medicament in dosage unit form" as used in this Specification means physically discrete coherent units suitable for medical administration each containing a daily dose or a multiple (up to four times) or submultiple (down to a fortieth) of a daily dose of the compound of the invention in association with a carrier and/or enclosed within an envelope. Whether the medicament contains a daily dose or, for example, a half, a third or a quarter of a daily dose will depend on whether the medicament is to be administered once or, for example, twice, three times or four times a day respectively.

The pharmaceutical composition according to the invention may, for example, take the form of ointments, gels, pastes, creams, sprays (including aerosols), lotions, suspensions, solutions and emulsions of the active ingredient in aqueous or non-aqueous diluents, syrups, granulates or powders.

The diluents to be used in pharmaceutical compositions (e.g. granulates) adapted to be formed into tablets, dragees, capsules and pills include the following: (a) fillers and extenders, e.g. starch, sugars, mannitol, and silicic acid; (b) binding agents, e.g. carboxymethyl cellulose and other cellulose derivatives, alginates, gelatine and polyvinyl pyrrolidone; (c) moisturizing agents, e.g. glycerol; (d) disintegrating agents, e.g. agar-agar, calcium carbonate and sodium bicarbonate; (e) agents for retarding dissolution e.g. paraffin; (f) resorption accelerators, e.g. quaternary ammonium compounds; (g) surface active agents, e.g. cetyl alcohol, glycerol monostearate; (h) adsorptive carriers, e.g. kaolin and bentonite; (i) lubricants, e.g. talc, calcium and magnesium stearate and solid polyethyl glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in microencapsulated form together with one or several of the above-mentioned diluents.

The diluents to be used in pharmaceutical compositions adapted to be formed into suppositories can, for example, be the usual water-soluble diluents, such as polyethylene glycols and fats (e.g. cocoa oil and high esters (e.g. $C_{14}$-alcohol with $C_{16}$-fatty acid)) or mixtures of these diluents.

The pharmaceutical compositions which are ointments, pastes, creams and gels can, for example, contain the usual diluents, e.g. animal and vegetable fats, waxes, paraffins, starch, tragacanth, cellulose derivatives, polyethylene glycols, silicones, bentonites, silicic acid, talc and zinc oxide or mixtures of these substances.

The pharmaceutical compositions which are powders and sprays can, for example, contain the usual diluents, e.g. lactose, talc, silicic acid, aluminium hydroxide, calcium silicate, and polyamide powder or mixtures of these substances. Aerosol sprays can, for example, contain the usual propellants, e.g. chlorofluorohydrocarbons.

The pharmaceutical compositions which are solutions and emulsions can, for example, contain the customary diluents (with, of course, the above-mentioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils (for example ground nut oil), glycerol, tetrahydrofurfuryl alcohol, polyethylene glycols and fatty acid esters of sorbitol or mixtures thereof.

For parenteral administration, solutions and emulsions should be sterile, and, if appropriate, blood-isotonic.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitane esters), microcrystalline cellulose, aluminium methahydroxide, bentonite, agar-agar and tragacanth or mixtures thereof.

All the pharmaceutical compositions according to the invention can also contain colouring agents and preservatives as well as perfumes and flavouring additions (e.g. peppermint oil and eucalyptus oil) and sweetening agents (e.g. saccharin).

The pharmaceutical compositions according to the invention generally contain from 0.1 to 99.5% usually from 0.5 to 95% of the active ingredient by weight of the total composition.

In addition to a compound of the invention, the pharmaceutical compositions and medicaments according to the invention can also contain other pharmaceutically active compounds. They may also contain a plurality of compounds of the invention.

Any diluent in the medicaments of the present invention may be any of those mentioned above in relation to the pharmaceutical compositions of the present invention. Such medicaments may include solvents of molecular weight less than 200 as sole diluent.

The discrete coherent portions constituting the medicament according to the invention will generally be adapted by virtue of their shape or packaging for medical administration and may be, for example, any of the following: tablets (including lozenges and granulates), pills, dragees, capsules, suppositories and ampoules. Some of these forms may be made up for delayed release of the active ingredient. Some, such as capsules, include a protective envelope which renders the portions of the medicament physically discrete and coherent.

The preferred daily dose for administration of the medicaments of the invention is 2.5 g to 10 g of active ingredient.

The production of the above-mentioned pharmaceutical compositions and medicaments is carried out by any method known in the art, for example, by mixing the active ingredient(s) with the diluent(s) to form a pharmaceutical composition (e.g. a granulate) and then forming the composition into the medicament (e.g. tablets).

This invention further provides a method of combating the abovementioned diseases in warm-blooded animals, which comprises administering to the animals a compound of the invention alone or in admixture with a diluent or in the form of a medicament according to the invention.

It is envisaged that these active compounds will be administered perorally, parenterally (for example intramuscularly, intraperitoneally, subcutaneously and intravenously), rectally or locally, preferably parenterally and, especially, intravenously. Preferred pharmaceutical compositions and medicaments are therefore those adapted for administration such as parenteral administration. However, the active compounds of the invention can also be administered topically. Administration in the method of the invention is preferably parenteral administration.

In general it has proved advantageous to administer amounts of from 10 mg to 300 mg/kg, preferably 50 mg to 200 mg/kg of body weight per day to achieve effective results. Nevertheless, it can at times be necessary to deviate from those dosage rates, and in particular to do so as a function of the nature and body weight of the human or animal subject to be treated, the individual reaction of this subject to the treatment, the type of formulation in which the active ingredient is administered and the mode in which the administration is carried out, and the point in the progress of the disease or interval at which it is to be administered. Thus it may in some case suffice to use less than the above-mentioned minimum dosage rate, whilst other cases the upper limit mentioned must be exceeded to achieve the desired results. Where larger amounts are administered it can be advisable to divide these into several individual administrations over the course of the day.

The following Examples I-1 to -43 illustrate processes for the production of compounds used according to the present invention whereas Examples II-1 to -16 illustrate processes for the production of intermediates.

EXAMPLE 1

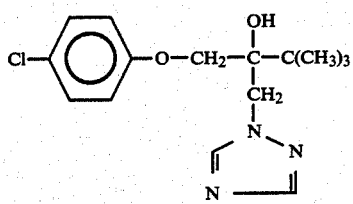
(I-1)

72.15 g (0.3 mole) of 2-(4-chlorophenoxy-methyl)-2-tert.-butyl-oxirane and 24.15 g (0.35 mole) of 1,2,4-triazole were heated under reflux in 120 ml of ethanol for 48 hours. The mixture was then concentrated, the residue was taken up in 200 ml ethyl acetate and the mixture was heated. It was then cooled in an ice-bath and the solid was filtered off and rinsed with ethyl acetate. The filtrate was concentrated, the residue was dissolved in ether/hexane and the solution was gassed with hydrogen chloride. The precipitate was filtered off and rinsed with ether, and the free base was obtained by adding ethyl acetate/1N sodium hydroxide solution. 60.2 g (65% of theory) of 2-(4-chlorophenoxy-methyl)-3,3-dimethyl-1-(1,2,4-triazol-1-yl)-butan-2-ol of melting point 84°-87° C. were obtained.

Preparation of the starting material (new intermediate produce of the formula (II))

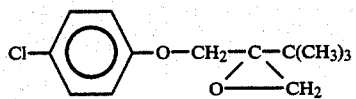

A solution of 162 ml (2.2 moles) of dimethyl sulphide in 400 ml of absolute acetonitrile was added to a solution of 189 ml (2.0 moles) of dimethyl sulphate in 1,200 ml of absolute acetonitrile at room temperature. The reaction mixture was stirred overnight at room temperature. 118.8 g (2.2 moles) of sodium methylate were then added. The mixture was stirred for 30 minutes and a solution of 272 g (1.2 moles) of 1-(4-chlorophenoxy)-3,3-dimethyl-butan-2-ene in 600 ml of absolute acetonitrile was then added dropwise in the course of 30 minutes. The reaction mixture was subsequently stirred overnight. It was then concentrated, the residue was partitioned between water and ethyl acetate, the organic phase was separated off, washed twice with water and once with saturated sodium chloride solution, dried over sodium sulphate and concentrated and the residue was distilled in vacuo. 242.4 g (84% of theory) of 2-(4-chlorophenoxy-methyl)-2-tert.-butyl-oxirane of boiling point 115°-22° C./0.003 mm Hg column and of melting point 50°-52° C. were obtained.

EXAMPLE 2

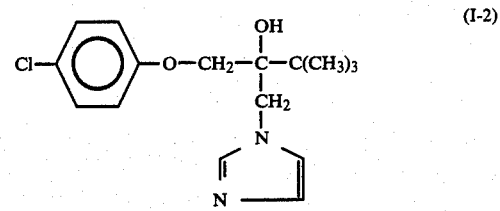
(I-2)

8.02 g (0.1178 mole) of imidazole were added to 2.71 g (0.1178 mole) of sodium in 250 ml of absolute ethanol. A solution of 14.17 g (0.0589 mole) of 2-(4-chlorophenoxy-methyl)-2-tert.-butyl-oxirane in 100 ml of ethanol was added dropwise at room temperature in the course of 30 minutes. The reaction mixture was then heated under reflux for 8 hours and concentrated and the residue was taken up in ether. The ether mixture was extracted three times with 1N hydrochloric acid and the combined hydrochloric acid phases were neutralised with sodium bicarbonate and then extracted with ethyl acetate. After concentrating the product phase and recrystallising the residue from cyclohexane, 11.6 g (64% of theory) of 2-(4-chlorophenoxy-methyl)-3,3-dimethyl-1-(imidazol-1-yl)-butan-2-ol of melting point 154°-55° C. were obtained.

EXAMPLE 3

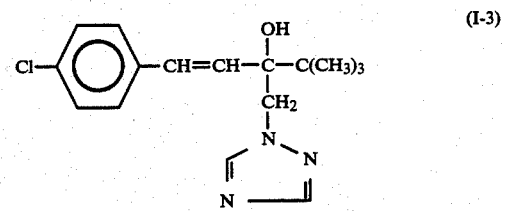
(I-3)

A solution of 17.75 g (0.075 mole) of 2-(4-chlorophenyl-ethenyl)-2-tert.-butyl-oxirane and 6.9 g (0.1 mole) of 1,2,4-triazole in 30 ml of ethanol were heated at 150° C. in a bomb tube for 20 hours. The reaction mixture was then concentrated and the crystalline residue was stirred with ether. The solid was then filtered off and recrystallised from acetonitrile. 17.7 g (77% of theory) of 1-(4-chlorophenyl)-4,4-dimethyl-3-(imidazol-1-yl-methyl)-1-penten-3-ol of melting point 139°-41° C. were obtained.

EXAMPLE 4

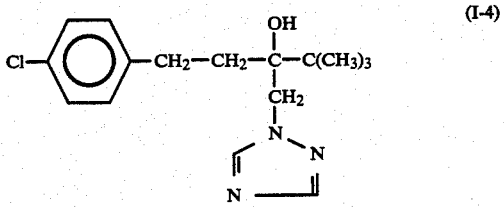
(I-4)

A solution of 17.9 g (0.075 mole) of 2-(4-chlorophenyl-ethyl)-2-tert.-butyl-oxirane and 6.9 g (0.1 mole) of 1,2,4-triazole in 30 ml of ethanol were heated at 150° C. in a bomb tube for 20 hours. The reaction mixture was allowed to cool and was concentrated. The residue was dissolved in ether and the ether solution was washed three times with water and once with sodium chloride solution, dried over sodium sulphate and concentrated. The residue was chromatographed over a silica gel column (mobile phase: methylene chloride/ethyl acetate 1:1). 12.3 g (53.2% of theory) of 1-(4-chlorophenyl)-4,4-dimethyl-3-(1,2,4-triazol-1-yl-methyl)-pentan-3-ol were obtained as a viscous oil.

The following compounds of the formula

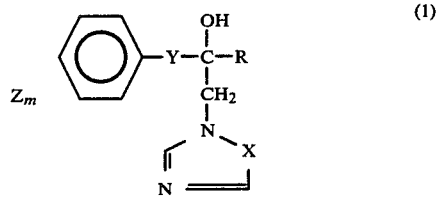

were obtained in an analogous manner by using corresponding molar amounts of reaction ingredients.

| Example No. | $Z_m$ | Y | R | X | Melting point (°C.) |
|---|---|---|---|---|---|
| I-5 | 4-Cl, 2-CH₃ | —O—CH₂— | —C(CH₃)₃ | N | 125.5-29 |
| 6 | 2,4-Cl₂ | —O—CH₂— | —C(CH₃)₃ | N | 120.5-23.5 |
| 7 | 4-CH₃ | —O—CH₂— | —C(CH₃)₃ | N | 98-101.5 |
| 8 | 2-CH₃ | —O—CH₂— | —C(CH₃)₃ | N | 89-101 |
| 9 | 4-F | —CH₂—CH₂— | —C(CH₃)₃ | N | 91-95.5 |
| 10 | 2-CH₃ | —CH=CH— | —C(CH₃)₃ | N | oil |
| 11 | 4-Cl | —CH₂—CH₂— | —C(CH₃)₃ | N | 212 (decomposition) (xHCl) |
| 12 | 2,4-Cl₂ | —O—CH₂— | —C(CH₃)₃ | CH | 152-54 |
| 13 | 4-CH₃ | —O—CH₂— | —C(CH₃)₃ | CH | 129-31 |
| 14 | 2-CH₃ | —O—CH₂— | —C(CH₃)₃ | CH | 123-24 |
| 15 | 4-Cl, 2-CH₃ | —O—CH₂— | —C(CH₃)₃ | CH | 157-59 |
| 16 | 4-Cl | —CH₂—CH₂— | —C(CH₃)₃ | CH | 157.5-59.5 |
| 17 | 4-F | —CH₂—CH₂— | —C(CH₃)₃ | CH | 124-25 |
| 18 | 2-CH₃ | —CH₂—CH₂— | —C(CH₃)₃ | CH | 94-99 |
| 19 | 4-Cl | —CH=CH— | —C(CH₃)₃ | CH | 158.5-62 |
| 20 | 4-F | —CH=CH— | —C(CH₃)₃ | CH | 144-46 |
| 21 | 2-CH₃ | —CH=CH— | —C(CH₃)₃ | CH | 127-32 |
| 22 | 4-Cl | —O—CH₂— | —⟨Ph⟩—Cl | CH | 216-17 |
| 23 | 4-CH₃ | —CH=CH— | —C(CH₃)₃ | N | 117-19 |
| 24 | 4-CH₃ | —CH=CH— | —C(CH₃)₃ | CH | 144-46 |
| 25 | 2,6-Cl₂ | —CH=CH— | —C(CH₃)₃ | CH | 110-16 |
| 26 | 4-CH₃ | —CH₂—CH₂ | —C(CH₃)₃ | N | oil |
| 27 | 2,4-Cl₂ | —CH₂—CH₂— | —C(CH₃)₃ | CH | 118-19 |
| 28 | 4—⟨Ph⟩ | —C—CH₂— | —C(CH₃)₃ | CH | 169-70.5 |
| 29 | 2-Cl | —O—CH₂— | —C(CH₃)₃ | CH | 122-24 |
| 30 | 2-Cl | —O—CH₂— | —C(CH₃)₃ | N | 109-11 |
| 31 | 2,4-Cl₂ | —CH₂—CH₂— | —C(CH₃)₃ | N | 94-95 |
| 32 | 2-CH₃ | —CH₂—CH₂— | —C(CH₃)₃ | N | 82-83 |
| 33 | 4-Cl | —O—CH₂— | Cl,Cl-⟨Ph⟩ | CH | 134-35.5 |
| 34 | 4—⟨Ph⟩— | —O—CH₂— | —C(CH₃)₃ | N | 118-19.5 |
| 35 | 4-Cl | —O—CH₂— | —⟨Ph⟩—Cl | N | 85-85 |
| 36 | 4-Cl | —O—CH₂— | Cl,Cl-⟨Ph⟩ | N | 149-51 |
| 37 | 4-F | —O—CH₂— | —C(CH₃)₃ | CH | 141-42 |
| 38 | 4-F | —O—CH₂— | —C(CH₃)₃ | N | 73-75 |
| 39 | 3-Cl | —O—CH₂— | —C(CH₃)₃ | CH | 124 |
| 40 | 2-Cl, 4-F | —O—CH₂— | —C(CH₃)₃ | CH | 137 |
| 41 | 3-Cl | —O—CH₂— | —C(CH₃)₃ | N | 72 |
| 42 | 2-Cl, 4-F | —O—CH₂— | —C(CH₃)₃ | N | 130 |

-continued

| Example No. | $Z_m$ | Y | R | X | Melting point (°C.) |
|---|---|---|---|---|---|
| 43 | 3,4-Cl$_2$ | —O—CH$_2$— | —C(CH$_3$)$_3$ | H | 124 |
| 44 | 4-CH$_3$ | —CH$_2$—CH$_2$— | —C(CH$_3$)$_3$ | CH | 101-03 |
| 45 | 4-F | —CH=CH— | —C(CH$_3$)$_3$ | N | 129-31 |
| 46 | 4-—Cl | —O—CH$_2$— | —C(CH$_3$)$_3$ | CH | 174-76 |
| 47 | 4-—Cl | —O—CH$_2$— | —C(CH$_3$)$_3$ | N | 109-11 |
| 48 | — | —O—CH$_2$— | —C(CH$_3$)$_3$ | N | 84-85 |
| 49 | 4-OCH$_3$ | —O—CH$_2$— | —C(CH$_3$)$_3$ | N | 63-66 |
| 50 | 4-C(CH$_3$)$_3$ | —O—CH$_2$— | —C(CH$_3$)$_3$ | N | 75-78 |
| 51 | 4-OCF$_3$ | —O—CH$_2$— | —C(CH$_3$)$_3$ | N | $n_D^{20} = 1,4902$ |

The following intermediate products of the formula (II),

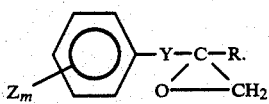

were obtained according to Example 1 using corresponding molar amounts of ingredients:

| Example No. | $Z_m$ | Y | R | Boiling point (°C.)/ mm Hg column |
|---|---|---|---|---|
| II-2 | 2,4-Cl$_2$ | —O—CH$_2$— | —C(CH$_3$)$_3$ | 125-27/0,3 |
| II-3 | 4-CH$_3$ | —O—CH$_2$— | | 85/0,07 |
| II-4 | 2-CH$_3$ | —O—CH$_2$— | | 89/0,07 |
| II-5 | 4-Cl,2-CH$_3$ | —O—CH$_2$— | | 114-17/0,33 |
| II-6 | 4-Cl | —CH$_2$—CH$_2$— | | 99-103/0,005 |
| II-7 | 2,4-Cl$_2$ | —CH$_2$—CH$_2$— | | 79/0,004 |
| II-8 | 4-F | —CH$_2$—CH$_2$— | | 79-89/0,003 |
| II-9 | 4-CH$_3$ | —CH$_2$—CH$_2$— | | 74-78/0,003 |
| II-10 | 2-CH$_3$ | —CH$_2$—CH$_2$— | | 95/0,005 |
| II-11 | 4-Cl | —CH=CH— | | melting point 61-62,5 |
| II-12 | 2,4-Cl$_2$ | —CH=CH— | | not isolated |
| II-13 | 4-CH$_3$ | —CH=CH— | | not isolated |
| II-14 | 4-F | —CH=CH— | | 75/0,005 |
| II-15 | 2-CH$_3$ | —CH=CH— | | 71-74/0,01 |
| II-16 | 2,6-Cl$_2$ | —CH=CH— | | not isolated |

The following Examples illustrate the in vivo and in vitro activity of compounds used in the present invention. In these Examples the compounds given below were employed as comparison substances:

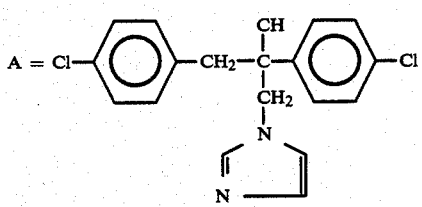

1,2-bis(4-chlorophenyl)-3-(imidazol-1-yl)-2-propanol

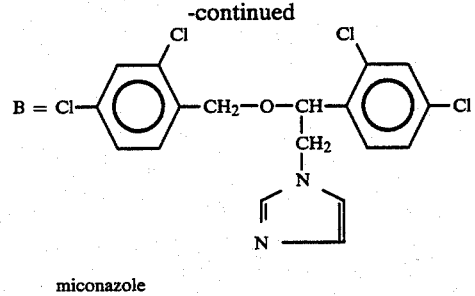

miconazole

EXAMPLE A

Antimycotic in vitro activity

Description of the experiment:

The in vitro test was carried out in a series dilution test using germ inocula of an average $5 \times 10^4$ germs/ml of substrate. The nutrient medium used was (A) for dermatophytes and moulds: Sabouraud's milieu d'épreuve and (B) for yeasts: isotonic sensitest broth from Oxoid.

The incubation temperature was 18° C.; the incubation period was 24 hours in the case of yeasts and 96 hours in the case of dermatophytes and moulds.

In this test, the compounds of Examples 1, -2, -5, -6, -7, -9, -12, -15, -16, -17, -18 and -19, for example, exhibited a better antimycotic action than the compound (A) known from the state of the art.

EXAMPLE B

Antimicrobial in vivo activity (oral) in Candidosis of mice

Description of the experiment:

Mice of the SPF-CF$_1$ type were infected intravenously with $1-2 \times 10^6$ logarithmically growing Candida cells, which were suspended in physiological sodium chloride solution. The animals were treated orally with in each case 50 to 100 mg of the formulation/kg of body weight one hour before and seven hours after infection.

Result:

Untreated animals died 3 to 6 days after infection. The survival rate on the 6th day after infection was about 5% in the case of untreated control animals.

In this test, for example, compounds of Examples I-1, -6, -16 and -19 exhibited an action ranging from moderate to very good, whilst the compound (B) known from the prior art showed no action.

EXAMPLE C

Antimicrobial in vivo activity (local) using the model of experimental trichophytosis in guinea pigs Description of the experiment:

White guinea pigs of the Pirbright-white strain were infected, on their shaven, non-scarified backs, with a microconidia and macroconidia suspension of *Trichophyton mentagrophytes.*

The infected animals were treated locally, once daily, with a 1% strength solution of the formulations according to the invention (in dimethylsulphoxide:-glycerol=1:4), starting on the 3rd day after infection.

Result:

The typical pattern of dermatophytosis with reddening, scaling and lose of hair up to total integumentary defect at the point of infection developed in the untreated animals with 12 days after infection.

In this test, compounds of Examples I-1, -2, -6, -12, and -15, for example, exhibited a good to very good action, that is to say no indication of infection on the 12th to 15th day after infection, or only slight reddening and isolated cases of scaling.

What is claimed is:

1. A method of combating mycoses in warm-blooded animals which comprises administering to the animals an antimycotically effective amount of a compound which is a 1-hydroxyethyl-azole derivative of the formula

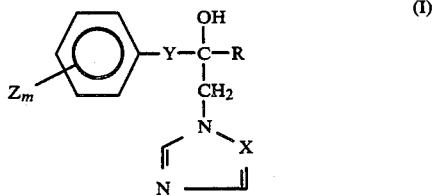

or a physiologically acceptable acid addition salt thereof, in which

R represents a $C_1$–$C_8$-alkyl radical, a $C_3$–$C_7$-cycloalkyl radical optionally substituted by $C_1$–$C_2$-alkyl or a phenyl radical optionally substituted by halogen, $C_1$–$C_4$-alkyl or halogenoalkyl with 1 or 2 carbon atoms and 1 to 5 halogen atoms, X represents a nitrogen atom or a CH group, Y represents a grouping —$CH_2CH_2$—, each Z independently represents a halogen atom, a $C_1$–$C_8$-alkyl, $C_3$–$C_7$-cycloalkyl, $C_1$–$C_8$-alkoxy, $C_1$–$C_8$-alkylthio, halogenoalkyl or halogenoalkoxy or halogenoalkylthio radical each of said halogen-atom-containing radicals having 1 to 2 carbon atoms and 1 to 5 halogen atoms, a phenyl radical, a phenoxy radical, a phenylalkyl radical or a phenylalkoxy radical, each of 7–8 C atoms and each being optionally substituted by halogen, $C_1$–$C_4$-alkyl or halogenoalkyl with 1 to 2 carbon atoms and 1 to 5 halogen atoms and m is 0, 1, 2 or 3 either alone or in admixture with a diluent or in the form of a medicament.

2. A method according to claim 1, in which the active ingredient is a compound as defined in claim 1 in which R represents a tert.-butyl, isopropyl or methyl radical; a cyclopropyl, cyclopentyl or cyclohexyl radical (in each case optionally methyl-substituted) or a phenyl radical which is optionally monosubstituted or disubstituted by fluorine, chlorine, methyl or trifluoromethyl; each Z independently represents a fluorine, chlorine or bromine atom or a methyl, tert.-butyl, cyclohexyl, methoxy, methylthio, trifluoromethyl, trifluoromethoxy or trifluoromethylthio radical, or a phenyl, phenoxy, benzyl or benzyloxy radical, (in each case optionally monosubstituted or disubstituted by fluorine, chlorine or methyl) and X, Y and m have the same meanings as in claim 1.

3. A method according to claim 1 wherein the 1-hydroxyethyl-azole derivative is 2-(4-chlorophenethyl)-3,3-dimethyl-1-(imidazol-1-yl)-butan-2-ol.

4. A method according to claim 1 in which the active compound is administered in an amount of 10 to 300 mg per kg body weight per day.

5. A method according to claim 1 in which the active compound is administered in an amount of 50 to 200 mg per kg body weight per day.

6. A method according to claim 1 in which the active compound is administered parenterally.

* * * * *